United States Patent [19]

Lanham, Jr. et al.

[11] Patent Number: 4,768,376

[45] Date of Patent: Sep. 6, 1988

[54] POLYETHYLENE COATING ADHESION TESTING

[75] Inventors: Robert L. Lanham, Jr., Mobile, Ala.; William F. Muller, Cornwall, N.Y.; Kenneth E. Paulhamus, Watsontown, Pa.; Joe L. Kinsey, Jr., Mobile, Ala.

[73] Assignee: International Paper Company, Purchase, N.Y.

[21] Appl. No.: 62,979

[22] Filed: Jun. 17, 1987

[51] Int. Cl.⁴ ............................................. G01N 19/04
[52] U.S. Cl. .................................. 73/150 A; 73/37.7; 73/49.8; 73/827
[58] Field of Search ................ 73/150 A, 150 R, 37.7, 73/38, 827

[56] References Cited

U.S. PATENT DOCUMENTS

| | | |
|---|---|---|
| 2,453,338 | 11/1948 | Pajak . |
| 2,694,924 | 11/1954 | Matlock . |
| 2,799,156 | 7/1957 | Southwick . |
| 2,885,892 | 5/1959 | Coutts . |
| 3,251,218 | 5/1966 | Russell . |
| 3,389,463 | 6/1968 | Gerek . |
| 3,396,578 | 8/1968 | Skundberg ...................... 73/150 A |
| 4,393,699 | 7/1983 | Seiler, Jr. .......................... 73/150 A |
| 4,491,014 | 1/1985 | Seiler, Jr. . |
| 4,567,758 | 2/1986 | Fisher . |

FOREIGN PATENT DOCUMENTS 0097551  5/1986  Japan ............................... 73/150 A Primary Examiner—Daniel M. Yasich
Attorney, Agent, or Firm—Walt Thomas Zielinski

[57] ABSTRACT

A method and an apparatus for testing the adhesion between the polyethylene coating and paperboard stock of polyethylene coated paperboard stock, such stock typically used in forming milk and fruit juice cartons. A normally open ended pressure chamber is closed by clamping a piece of polyethylene coated paperboard over its open end. The coating facing the pressure chamber is cut completely through to form an opening. Air of a predetermined value is introduced into the pressure chamber. The opposite coating will form a bubble, indicating delamination, if the integrity of the adhesion between the polyethylene coating and the paperboard is poor. The air pressure at which delamination occurs is then used to quantify adhesion.

7 Claims, 2 Drawing Sheets

POLYETHYLENE COATING ADHESION TESTING

BACKGROUND OF THE INVENTION

This invention relates to a method and apparatus for the testing of the adhesion between the polyethylene coating and the paperboard stock of polyethylene coated paperboard stock of type typically used for the manufacture of milk and fruit juice cartons. In the manufacture of such cartons, it is often desirable to test the quality of adhesion between the extruded polyethylene coating on the paperboard and the paperboard. Prior to this invention, the industry has lacked a satisfactory test for evaluating this adhesion. Prior practice required searching for weak adhesion areas with a very unreliable and and subjective knife technique.

SUMMARY OF THE INVENTION

According to the practice of this invention, the adhesion between a thermoplastic coating, typically polyethylene, on paperboard stock and the paperboard stock is determined by use of pressurized air. The invention makes use of the porous nature of the paperboard stock. In carrying out the invention, a sample of the paperboard stock, such as taken from a coating apparatus after the polyethylene has been extruded on both sides of the stock, is cut on one of the coated surfaces to thereby define an opening extending completely through the coating. The sample then is placed over the open end of a pressure chamber, to thereby close the pressure chamber. The other side of the paperboard is clamped. Pressurized air now is introduced into the pressure chamber. The air from the pressure chamber passes through the opening in the polyethylene coating and into the paperboard. The paperboard is porous with result that the pressurized air passes through the paperboard. The air passing through the paperboard travels in a direction parallel with the paperboard, and also in a direction at right angles thereto. Thus, there is an air force urging the opposite polyethylene coating away from the paperboard, this sometimes causing a delamination between this opposite coating and the paperboard. For a quality of adhesion which is acceptable, there will be no delamination for a given air pressure. However, if there is a less than acceptable quality of adhesion between the polyethylene coating and the paperboard, then delamination will occur. The pressure of the pressurized air may be readily measured, so that a numerical correlation may be made between the air pressure and delamination, thus making it possible to quantify adhesion as well as to locate and reveal weak adhesion areas rapidly and objectively.

DESCRIPTION OF THE INVENTION

Figure 1:
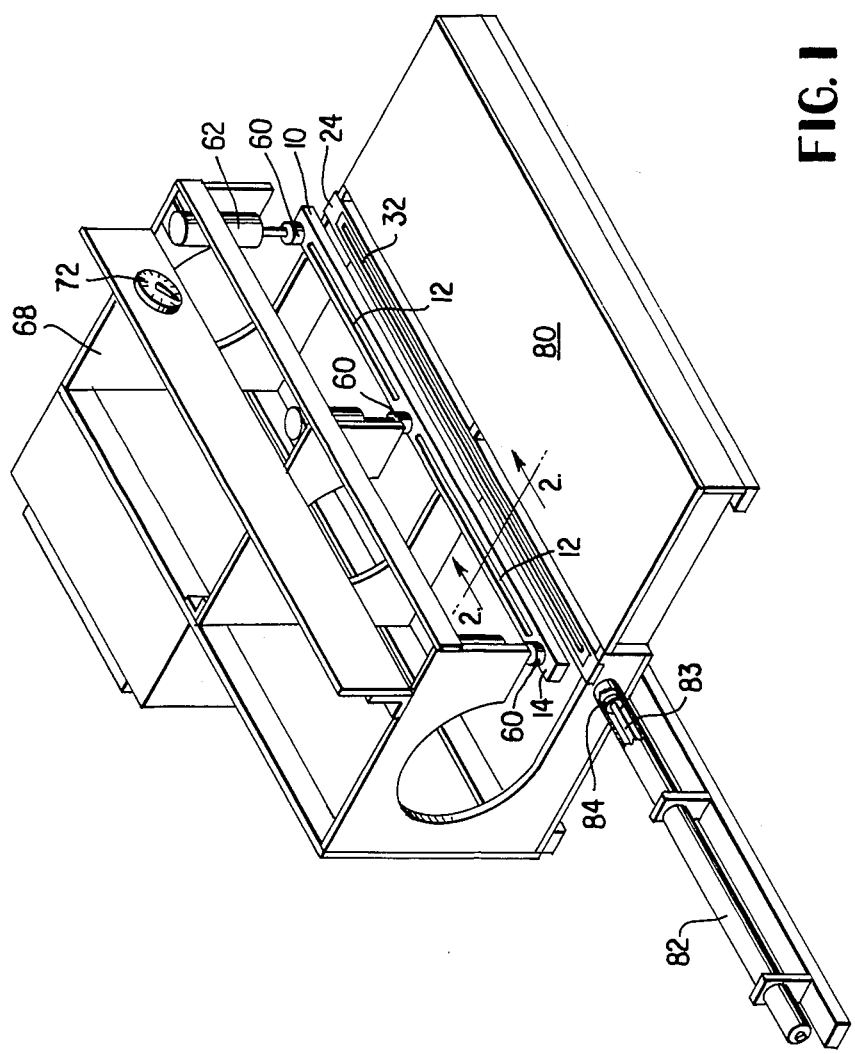
FIG. 1 is a perspective view illustrating an apparatus for carrying out the invention.
Figure 2:
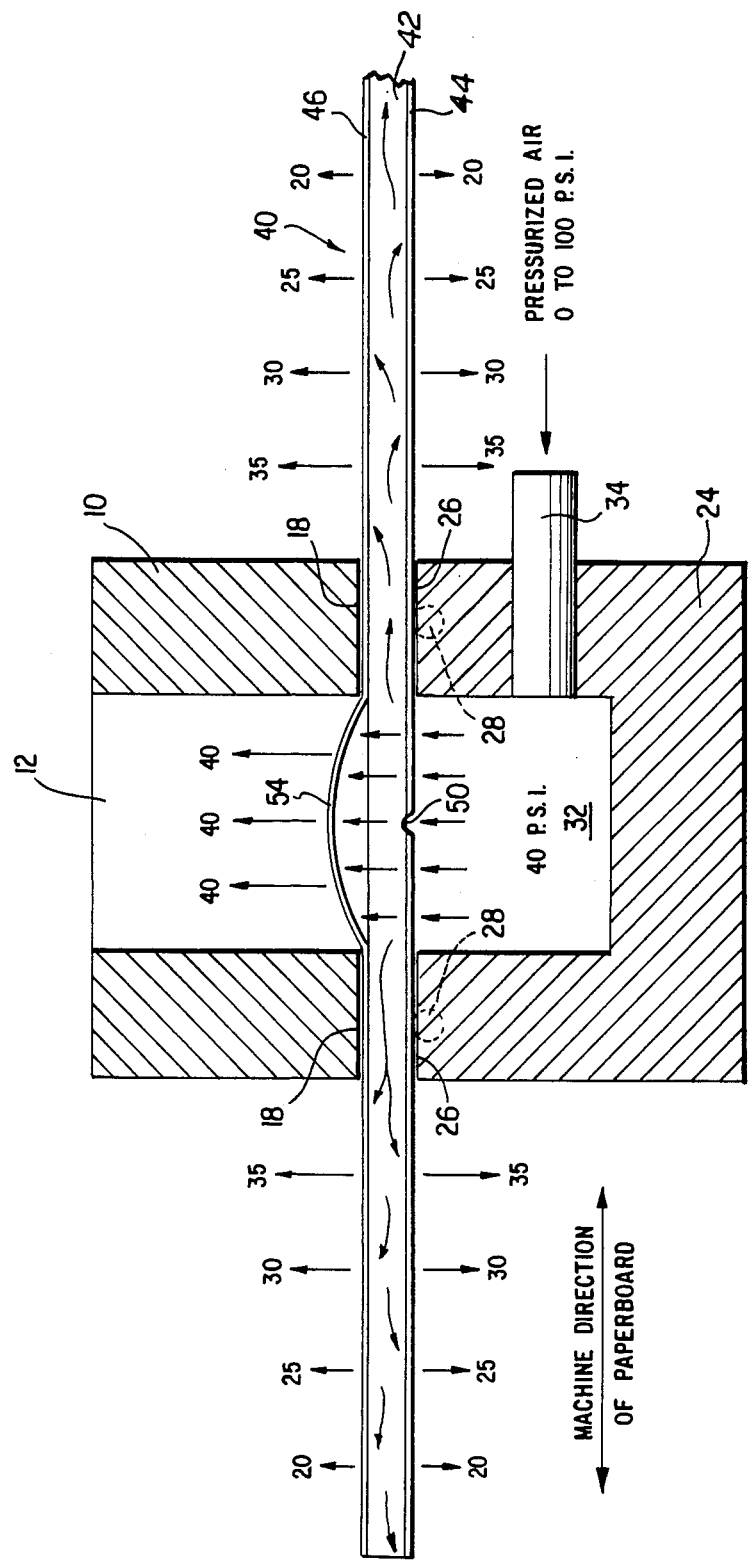
FIG. 2 is a view taken along section 2—2 of FIG. 1 and also illustrates the method of carrying out the invention.

Referring now particularly to FIG. 2, the numeral 10 denotes generally a clamping bar, termed an upper clamping bar for purposes of description. The clamping bar is generally elongated and carries a through opening, generally vertically extending, and denoted by the numeral 12. Opening 12 is generally elongated, and there may be more than one opening 12 in clamping bar 10, as indicated at FIG. 1. Also as indicated in FIG. 1, the longitudinal ends of openings 12 are closed, with these closed portions being secured to movable portions 60 of pneumatic cylinders 62 for raising and lowering the clamping bar 10. Cylinders 62 are mounted on a frame member denoted by the numeral 68. The numeral 18 in FIG. 2 denotes the lower clamping surfaces of clamping bar 10. The numeral 24 denotes an elongated housing complementary in size and shape to clamping bar 10, and having a pair of spaced clamping surface portions 26, also elongated and complementary to portions 18 of bar 10. Air tight seal elements, such as O-rings 28, are provided in the lower clamping surfaces 26. The numeral 32 denotes an air pressure chamber cavity defined by the walls of housing 24, with numeral 34 indicating an intake to the pressure chamber 32 from a source of air pressure. The cavity 32 may typically be 24 inches long and 0.5 inches wide.

The numeral 40 denotes a piece of paperboard stock coated on both of sides with a thermoplastic coating, the latter typically formed by extruded polyethylene. The thickness of the paperboard and its coatings is greatly exaggerated for purposes of illustration. The numeral 42 denotes the paperboard itself, the numeral 44 denoting the lower polyethylene coating, while the numeral 46 denotes the upper polyethylene coating. The upper coating 46 faces away from the pressure chamber 32 while lower coating 44 faces the chamber. The numeral 50 denotes an opening in the lower coating 44. As will be explained with the connection with FIG. 1, opening 50 may be made by a linearly reciprocating carbide tipped cutter acting along cavity 32 for forming the elongated slit or slot 50.

A sample of the coated paperboard stock is placed between the upper clamping bar 10 and the pressure chamber 24. Thus, the upper clamping portions 18 and lower clamping portions 26 clamp the respective surfaces of coated paperboard piece 40 and thereby define a substantially continuous peripheral clamping zone.

The up and down motion of the clamping bar 10 is carried out by the actuation of pneumatic cylinders 62 which are shown in FIG. 1. After the coated paperboard piece 40 has been clamped, seal 28 cooperates with the clamping surface 26 and the clamped paperboard piece to define a substantially air tight continuous annular zone. The lower face of 18 of the clamping bar 10 is also substantially annularly continuous. Then, pressurized air is introduced into cavity 32. As indicated by the curved arrows within paperboard 42, the porosity of the paperboard permits the pressurized air to escape from the edges of the paperboard piece. Assuming a typical pressure of 40 psi in cavity 32, this air passes through opening 50 and then outwardly along the path of the curved arrows, with the pressure decreasing with distance from the clamping zone as indicated by the vertically extending arrows. A portion of the air entering paperboard 42 from opening 50 will press against portion 54 of the upper coating 46. If the adhesion between the upper surface of paperboard 42 and the lower surface of upper coating 46 is less than a predetermined amount or predetermined standard, then there will be a delamination, with the result that a bubble will form. This bubble is indicated in FIG. 2 by the numeral 54 and may be observed by looking down into the top of the cavities 12. High pressure in the paperboard forces weakly adhered polyethylene away from the paperboard.

Referring again to FIG. 1, the numeral 72 denotes a pressure gauge to measure the pressure within cavity 32 of the pressure chamber. The numeral 80 denotes a table upon which a sample piece of the coated paperboard may be placed for insertion between the upper clamping bar 10 and lower pressure chamber 24. The numeral 82 denotes a housing which receives an elongated rod 83, indicated by the broken section of housing 82 in FIG. 1, the rod in turn carrying a carbide coating cutting element 84. The cutting element extends to the level of clamping surfaces 26 of pressure chamber 24, for the purpose of making opening 50, the opening being an elongated slit or slot formed by the cutter. The cutter may be actuated by air to move from one end to the other end of pressurized cavity 32. It will be understood, however, that the opening 50 need not be in the form of an elongated slit or slot and, further, need not be formed after the sample piece has been clamped by upper clamping bar 10. In this latter mode of practicing the invention, the housing 82 and cutter 84 within it are not required. The slot 50 may then be formed manually. The opening 50 may assume a variety of forms and may be formed in the sample piece before it is placed in the testing apparatus. If desired, the operation of the pneumatic cylinders 62, the clamping bar 10 and the cutter 84 may be automated, although such a system/control forms no part of this invention, the described invention being capable of being practiced without being automated.

As indicated in FIG. 2 of the drawings, the machine direction of the coated paperboard stock sample is preferably in a direction at right angles to the longitudinal axis of the clamping bar 10 and housing 24. As also indicated in FIG. 2, the range of (guage) pressure may be from zero to 100 psi.

What is claimed is:

1. A method of testing the adhesion of thermoplastic coating on thermoplastic coated paperboard stock, the paperboard stock being porous and being coated on both sides thereof, the method including the steps of, clamping both sides of a piece of thermoplastic coated paperboard stock to define an at least substantially continuous annular clamping zone on both sides of said paperboard stock, forming a pressure chamber on one side of said paperboard stock, with the paperboard stock within the confines of said annular clamping zone defining one wall of said pressure chamber, one of the two coated surfaces of said paperboard facing said pressure chamber, and the other of said two coated surfaces facing away from said pressure chamber, forming an opening through that one thermoplastic coating which faces said chamber, admitting air at a predetermined, above ambient pressure to said pressure chamber to thereby permit air from the pressure chamber to enter the paperboard through said opening, observing whether or not the other thermoplastic coating, which faces away from the pressure chamber, separates from the paperboard stock at said predetermined, above ambient pressure, whereby the quality of the adhesion between the thermoplastic coating and the paperboard can be correlated with the value of the predetermined, above ambient pressure to thereby quantify adhesion, by observing said separation or non-separation at the predetermined pressure.

2. The method of claim 1 wherein said thermoplastic coating is polyethylene.

3. The method of claim 1 wherein the step of forming an opening through the thermoplastic coating is carried out by cutting a slit in the thermoplastic coating after said clamping step.

4. The method of claim 1 including the additional step of sealing, by an O-ring seal between the pressure chamber and that coating which faces the pressure chamber, said annular clamping zone, on at least to thereby produce an air tight clamping zone on said piece of paperboard stock.

5. An apparatus for testing the adhesion of thermoplastic coating on a thermoplastic two sided coated piece of porous paperboard stock, the apparatus including a lower, open ended pressure chamber, the chamber having a conduit leading to it for the introduction of pressurized air, the open end of said pressure chamber being at least substantially annularly continuous, an upper clamping bar having an opening therethrough, the clamping bar opening corresponding in size and shape to the opening of the open ended pressure chamber, the lower periphery of the upper clamping bar opening being aligned with the periphery of the pressure chamber opening and being spaced therefrom, means to move said clamping bar towards and away from said pressure chamber, whereby a piece of thermoplastic coated paperboard having an opening in that said thermoplastic coating which faces the pressure chamber can be clamped between said two peripheries to thereby close the open end of said pressure chamber and pressurized air admitted to said pressure chamber, pressurized air in the chamber entering said coating opening, to test the adhesion of the thermoplastic coating to said paperboard stock.

6. The apparatus of claim 5 wherein said pressure opening periphery is provided with a seal therearound.

7. The apparatus of claim 5 including a linearly reciprocable cutter within said pressure chamber, whereby the cutter can cut an opening in a thermoplastic coating on that side of said piece of the thermoplastic coated paperboard stock which is adapted to be clamped between said two peripheries.

* * * * *